United States Patent [19]

Fishman

[11] 4,250,326
[45] Feb. 10, 1981

[54] METHOD OF REDUCING THE CONTENTS OF HALOETHYNYL-CONTAINING IMPURITIES IN SYNTHETIC DIHALOETHENYL PYRETHROID INSECTICIDES OR INTERMEDIATES BY REACTION WITH PHOSPHITES

[75] Inventor: Morris L. Fishman, East Windsor, N.J.

[73] Assignee: FMC Corporation, Philadelphia, Pa.

[21] Appl. No.: 87,273

[22] Filed: Oct. 22, 1979

[51] Int. Cl.$^3$ ................... C07B 21/00; C07C 69/743
[52] U.S. Cl. .............................. 560/124; 260/326.32; 260/340.5 R; 260/346.22; 260/347.2; 260/347.4; 260/465 D; 260/941; 260/969; 260/464; 260/346.73; 549/41; 549/57; 549/62; 549/66; 549/75; 549/79; 549/58; 549/60; 549/65; 549/77

[58] Field of Search ................... 560/124; 260/326.32, 260/340.5 R, 346.22, 347.2, 347.4, 465 D; 549/41, 57, 62, 66, 75, 79

[56] References Cited

U.S. PATENT DOCUMENTS 4,024,163  5/1977  Elliott ................................. 560/124

*Primary Examiner*—Natalie Trousof
*Assistant Examiner*—Michael Shippen
*Attorney, Agent, or Firm*—Robert M. Kennedy; Robert L. Andersen; H. Robinson Ertelt

[57] ABSTRACT

A method of reducing the content of a haloethynyl-containing impurity in a synthetic dihaloethenylcyclopropanecarboxylate by treatment with a phosphite under condition allowing the haloethynyl-containing impurity and phosphite to chemically interact, and thereafter recovering the dihaloethenylcyclopropanecarboxylate from the reaction mixture is disclosed.

12 Claims, No Drawings

METHOD OF REDUCING THE CONTENTS OF HALOETHYNYL-CONTAINING IMPURITIES IN SYNTHETIC DIHALOETHENYL PYRETHROID INSECTICIDES OR INTERMEDIATES BY REACTION WITH PHOSPHITES

The present invention relates to the general field of chemical manufacture. Specifically, it relates to the manufacture of synthetic pyrethroid insecticides, and more specifically to the purification of a synthetic dihaloethenylcyclopropanecarboxylate insecticide or intermediate contaminated with the corresponding haloethynylcyclopropanecarboxylate, by treatment with a phosphite under conditions allowing the haloethynyl-containing impurity and phosphite to chemically interact, and thereafter recovering the dihaloethenylcyclopropanecarboxylate from the reaction mixture.

Pyrethrins, naturally occurring extracts of chrysanthemum flowers, have long been of interest as insecticides. Since elucidation of the structures of these compounds, synthesis efforts have been directed toward preparation of related compounds having enhanced insecticidal activity and improved stability toward air and light. A noteworthy advance in this area was the discovery by Elliott et al. of certain highly active dihaloethenylcyclopropanecarboxylates such as the commercial insecticide permethrin, the common name for 3-phenoxybenzyl 3-(2,2-dichloroethenyl)-2,2-dimethylcyclopropanecarboxylate. This class of compounds is set forth in U.S. Pat. No. 4,024,163, issued May 17, 1977. The combined qualities of increased photostability and generally high insecticidal activity possessed by compounds of the dihaloethenyl class of pyrethroid insecticides, particularly permethrin, led to the development of a number of chemical processes for producing them. A number of such processes are described in *Synthetic Pyrethroids*, ACS Symposium Series, No. 42, M. Elliott, Ed., American Chemical Society, Washington, D.C., 1977, particularly chapters 4, 10, and 12. Of especial interest and commercial importance is the Sagami process described in *Synthetic Pyrethroids*, supra, and set forth in Belgian Pat. No. 833,278.

In the Sagami process a dihaloethenylcyclopropanecarboxylate is produced by base induced double dehydrohalogenation of certain 4,6,6,6-tetrahalohexanoates. The crude product so produced usually contains in addition to the desired dihaloethenylcyclopropanecarboxylate, a small amount, usually about 3–4%, of the corresponding haloethynylcyclopropanecarboxylate as a by-product. The reaction of the Sagami process is illustrated by the chemical equation below wherein X represents a halogen atom and R represents any of certain alcohol residues.

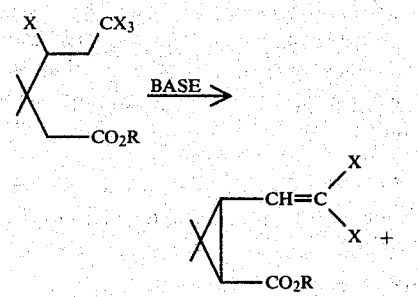

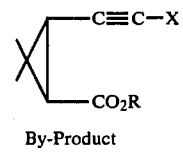

By-Product

Generally, various amounts of a haloethynyl compound may result whenever a dihaloethenyl compound having a hydrogen on the α-carbon of the ethenyl group is placed in a basic pH environment. For example, a haloethynyl by-product may be formed when a dihaloethenylcyclopropanecarboxylate is subjected to a base effected transesterification, alcoholysis, or hydrolysis reaction.

A commonly used procedure for purifying many of such haloethynyl contaminated dihaloethenylcyclopropanecarboxylates is distillation. However, the boiling point of the haloethynyl by-product is frequently sufficiently close to the boiling point of the dihaloethenyl compound to render distillation an inefficient and only partially effective method of purification.

It has now been found that dihaloethenylcyclopropanecarboxylates contaminated with haloethynyl containing impurities can be effectively purified by first contacting the sample of dihaloethenyl compound to be purified with any of certain phosphites under conditions which allow the phosphite to react selectively with the haloethynyl impurity in a Michaelis-Arbuzov type chemical reaction, thereby reducing the content of haloethynyl impurity in the sample, and thereafter recovering the dihaloethenylcyclopropanecarboxylate from the reaction mixture, preferably by distillation.

The Michaelis-Arbuzov reaction is the name generally given for the reaction of an alkyl halide with a trialkyl phosphite to form a monoalkylphosphonate, by way of the phosphonium salt (*Merck Index*, Martha Windholz, Ed., Merck & Co., Inc., Rahway, N.J., 9th Edition, 1976 and references therein):

$R^1$ is usually an alkyl group, and X is a halogen atom.

Alkynyl halides ($R^1$ is an alkynyl group) are also known to react with phosphites in a Michaelis-Arbuzov fashion:

(a) Mashlykovskii and Ionin, Zh. Obshch. Khim., 35, 1577 (1965); C.A., 63, 18143d (1965):

(b) Zavgorodnni, Ionin, and Petrov, Zh. Obshch. Khim., 37, 949 (1967); C.A. 68, 39754c (1968):

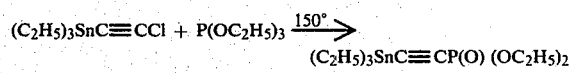

(c) Ionin and Petrov, Zh. Obshch. Khim., 32, 2387 (1962); C.A. 58, 9115b (1963):

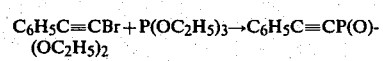

Compounds where $R^1$ is an alkenyl group normally do not react with phosphites in the absence of an activating group, such as an electron-withdrawing group in conjugation with the alkenyl group, or in the absence of special catalysts, such as nickel chloride or palladium chloride, and high temperatures; Tavs and Weitkamp, Tetrahedron, 26, 5529 (1970). The use of nickel chloride catalyst is exemplified in the Tavs and Weitkamp article by the following chemical equation:

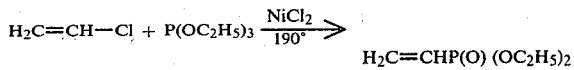

U.S. Pat. No. 2,920,097, issued to Frazza and Rapoport, Jan. 5, 1960 discloses the reaction of a trialkyl phosphite with a cyano activated alkenyl halide, beta-chloroacrylonitrile, as shown in the following chemical equation wherein R is an ethyl, propyl, or butyl group.

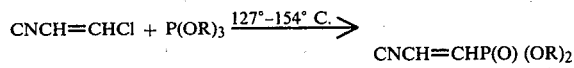

Kreutzkamp and Schindler have shown that an acetyl activated alkenyl halide is also a suitable substrate in a Michaelis-Arbuzov type reaction with tributyl phosphite [Chem. Ber., 92, 1697 (1959); C.A. 53, 21620c (1959)]:

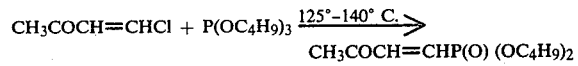

The unreactivity of alkenyl halides toward phosphites in the absence of activating groups or special catalysts formed the basis of a method of purifying vinylidine chloride ($CH_2=CCl_2$) contaminated with dichloroacetylene; disclosed in U.S. Pat. No. 3,751,495, issued to Seyferth, Aug. 7, 1973. In the Seyferth process, a phosphite, or any of certain other phosphorus derivatives, is allowed to react with the dichloroacetylene at from about room temperature to 50° C., usually in a pressure bottle, and the vinylidine chloride, which is unreactive toward the phosphorus containing reactant under the conditions employed, is separated from the reaction mixture by distillation. Vinylidine chloride is a simple alkenyl dihalide, and does not contain an activating group as do the slightly more complex alkenyl halides discussed above which undergo a Michaelis-Arbuzov reaction with phosphites.

Dihaloethenylcyclopropanecarboxylates, unlike vinylidine chloride, are complex organic molecules. In these compounds the dihaloethenyl group is chemically bonded to a cyclopropane ring to which an ester carbonyl group is also bonded. It has long been known that a cyclopropane ring can conjugate, in a manner somewhat analogous to a carbon-carbon double bond, with an olefin or a carbonyl group (Fieser and Fieser, *Advanced Organic Chemistry*, Reinhold Publishing Corp., New York, 1961, chapter 15, page 534). One might thus expect the ethenyl halogens of dihaloethenylcyclopropanecarboxylates to be "activated" for reaction with phosphites by the electron withdrawing effect of the ester carbonyl group, the electron withdrawal reaching the ethenyl halogens by virtue of a chain of conjugation of the ethenyl group, cyclopropane ring, and carbonyl group. It has not, however, been settled whether a cyclopropane ring can transmit the conjugation effects of contiguous unsaturated groups (see M. Charton in *The Chemistry of Alkenes*, J. Zabicky, Ed., Interscience Publishers, New York, 1970, chapter 10, particularly the discussion on pages 536 and 567, and the conclusory statements at the end of each subsection on pages 530-568). Thus, the question of whether the electron withdrawing ester carbonyl group would function as an activating group in dihaloethenylcyclopropanecarboxylates for Michaelis-Arbuzov type reactions with phosphites could not have been answered with a high degree of certainty prior to the present invention. One could not have predicted, based on the prior art considered as a whole, whether dihaloethenylcyclopropanecarboxylates would be reactive toward phosphites. The present invention obtains from applicant's discovery that certain dihaloethenylcyclopropanecarboxylates are unreactive toward phosphites under conditions where the corresponding haloethynylcyclopropanecarboxylates are reactive.

The present invention provides a process for reducing the content of a 3-(haloethynyl)cyclopropanecarboxylate impurity of the formula

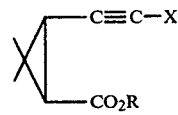

in a mixture containing the impurity and a 3-(2,2-dihaloethenyl)cyclopropanecarboxylate of the formula

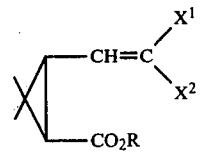

wherein $X^1$ and $X^2$ are the same or different, and each is a fluorine, chlorine, or bromine atom; X is a fluorine, chlorine, or bromine atom, and is the same as $X^1$ or $X^2$; and R is an alkyl group of 1 to 4 carbon atoms, preferably 1 or 2 carbon atoms, or is the residue $R^1$ of an alcohol $R^1OH$ which forms an insecticidal ester when combined with chrysanthemic acid, with the proviso that $R^1$ may not contain a haloalkyl or haloalkynyl group, which comprises contacting said mixture with a phosphite of the formula $P(OR^2)_3$ wherein the $R^2$ groups are the same or different and each is an alkyl group of 1 to 6 carbon atoms, preferably b 1 to 4 carbon atoms, or a phenyl group, so that the phosphite and haloethynyl impurity chemically interact, and thereafter recovering the dihaloethenylcyclopropanecarboxylate from the reaction mixture.

A wide range of alcohol residues $R^1$ the alcohol derivatives of which form insecticidal esters when combined with chrysanthemic acid are known in the art, for example, groups of the formulas

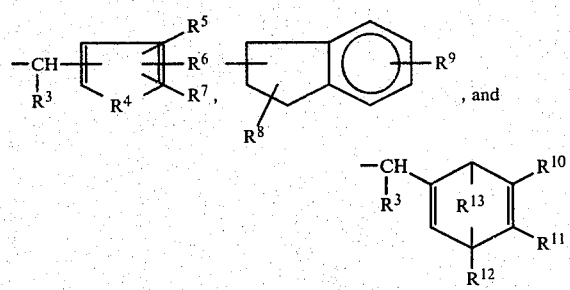 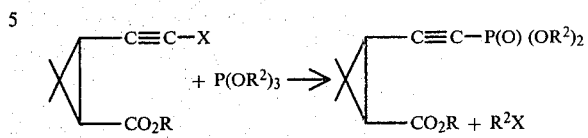

in which $R^3$ is hydrogen, lower alkyl, ethynyl, or cyano; $R^4$ is divalent oxygen, divalent sulfur, or vinylene; $R^5$, $R^6$, and $R^7$ are independently hydrogen, lower alkyl, halogen, lower alkenyl, phenyl, phenoxy, benzyl, phenylthio, or any two of $R^5$, $R^6$, and $R^7$ are joined to form a divalent methylenedioxy group attached to two adjacent ring carbon atoms of a phenyl ring, with the proviso that when $R^5$, $R^6$, or $R^7$ contains a phenyl ring such phenyl ring may be substituted with one to three substituents selected from halogen and lower alkyl; $R^8$ is hydrogen, lower alkyl, lower alkoxy, lower alkenyl, lower alkenyloxy, phenyl or benzyl; $R^9$ is hydrogen, halogen, lower alkyl, lower alkoxy, lower alkenyl, lower alkenyloxy, lower alkylthio, lower alkylsulfinyl, lower alkylsulfonyl, phenyl, phenoxy, benzoyl, nitro or cyano; $R^{10}$ and $R^{11}$, the same or different, are hydrogen, lower alkyl, halogen, cyano, lower alkyloxycarbonyl, or lower alkylaminocarbonyl; $R^{13}$ is an atom of oxygen or sulfur, N—$R^{14}$ where $R^{14}$ is hydrogen or lower alkyl, or a methylene group; and $R^{12}$ is phenyl, benzyl, or benzoyl, which may be substituted on the phenyl ring with halogen or lower alkyl.

Examples of such $R^1$ groups are 3-phenoxybenzyl, α-cyano-3-phenoxybenzyl, 5-benzyl-3-furylmethyl, 3-phenylbenzyl, 2,6-difluoro-3-phenylbenzyl, 2,6-dichloro-3-phenylbenzyl, 2-methyl-3-phenylbenzyl, 3-(3'-fluoro)phenylbenzyl, 4-phenyl-2-indanyl, 5-benzyl-2-thienylmethyl, and 2,3-bis(methoxycarbonyl)-4-phenylmethyl-7-oxabicyclo[2.2.1]hepta-2,4-diene-6-ylmethyl. Frequently $R^1$ will be 3-phenoxybenzyl, α-cyano-3-phenoxybenzyl, or 5-benzyl-3-furylmethyl.

The groups $X^1$ and $X^2$ will frequently be the same, and will usually be bromine or chlorine atoms.

It is generally advantageous to conduct the present process on a dihaloethenylcyclopropanecarboxylate which is an intermediate (R is alkyl) rather than a final product insecticide (R is $R^1$).

The present process may be used to remove or reduce the content of haloethynyl impurity in crude dihaloethenylcyclopropanecarboxylate which has not been subjected to a prior purification process, or in impure dihaloethenylcyclopropanecarboxylate obtained from one or more prior purification steps which either reduced or increased the amount of haloethynyl impurity present. For example, forecuts from the distillation of crude dihaloethenylcyclopropanecarboxylate are usually enriched with the haloethynyl impurity. In some instances the forecuts may actually contain more of the haloethynyl compound than dihaloethenyl compound. The present process may suitably be employed to reduce the content of haloethynyl impurity in such batches of dihaloethenylcyclopropanecarboxylate containing a substantial quantity of the impurity.

It is expected that the reaction of phosphite with the haloethynyl impurity in the present invention will take the normal Michaelis-Arbuzov reaction course resulting in conversion of the haloethynyl compound to a phosphonate:

However, the actual nature of the reaction and the identity of the reaction products may be different from those just postulated and still be within the scope of the present invention. The inventive concept does not reside in a particular reaction mechanism or product, but in the selective reaction of a phosphite with the haloethynyl impurity to give a product from which the dihaloethenylcyclopropanecarboxylate may be readily separated.

In accordance with the present invention a mixture containing a dihaloethenylcyclopropanecarboxylate and the corresponding haloethynylcyclopropanecarboxylate is contacted with a phosphite, and the whole reaction mixture is heated at an elevated temperature, preferably in the range of about 125° to 175° C., more preferably 140° to 150° C., so that the phosphite and haloethynyl compound chemically interact. The reaction is usually complete in about 2 to 4 hours after addition of the phosphite under these preferred temperature conditions. The reaction is expected to proceed at lower temperatures, but at a much slower rate. Higher temperatures, up to the decomposition point of the phosphonate product of the reaction, may also be used. The phosphonate product where R is methyl or ethyl, and $R^2$ is methyl or ethyl undergoes a two step exothermic decomposition at about 200°–220° C. It is possible that the reaction of certain phosphites with a particular haloethynyl compound will produce a phosphonate product having a decomposition point below 200° C., and within the preferred reaction temperature range given above. In that event, the reaction temperature should be adjusted lower accordingly. Degradation of the phosphonate product may interfere with the subsequent recovery of the dihaloethenyl compound from the reaction mixture.

For optimum results the phosphite should be used in at least an equimolar amount, based on the amount of haloethynyl impurity in the starting mixture. It is usually desirable to employ a slight excess of phosphite. While phosphites having different $R^2$ groups, mixed phosphite esters, are useful in the present process, economic and commercial availability considerations will generally favor use of phosphites having all the $R^2$ groups the same.

The use of a solvent is not required in conducting the process of the present invention. However, inert solvents such as aromatic or aliphatic hydrocarbons, ethers, and the like may be used, but the selected solvent should have a boiling point within the suggested temperature range for conducting the reaction or higher. The use of a lower boiling solvent will necessitate conducting the reaction at a lower temperature, and may result in an inordinately long reaction period.

Upon completion of the reaction of the haloethynyl impurity and the phosphite, the dihaloethenylcyclopropanecarboxylate is recovered from the reaction mixture. The preferred method of recovering the dihaloethenyl compound is distillation, particularly where R is an alkyl group. Other general methods of separation, such as chromatography, may also be used.

The present invention is further described in the following examples, which are provided only by way of illustration and not of limitation. Unless otherwise specified, all temperatures are in degrees Celsius.

Examples 1 and 2 illustrate reaction of the haloethynyl impurity with a phosphite, and recovery of the unreacted dihaloethenyl compound from the reaction mixture by distillation. In Example 1 the process was conducted on a distillation forecut of the crude dihaloethenyl compound. The forecut contains a much higher percent of haloethynyl impurity than that present prior to distillation. In Example 2, the process was conducted on crude dihaloethenyl compound which had not been subjected to prior distillation.

EXAMPLE 1

Crude methyl 3-(2,2-dichloroethenyl)-2,2-dimethylcyclopropanecarboxylate was subjected to fractional distillation under vacuum, and lower boiling fractions were combined to give 2313 g of a forecut. The forecut was shown by gas liquid phase chromatography (glpc), area %, to contain 57% (1318 g) of methyl 3-(2,2-dichloroethenyl)-2,2-dimethylcyclopropanecarboxylate and 26% (3.2 moles) methyl 3-(chloroethynyl)-2,2-dimethylcyclopropanecarboxylate.

The forecut was heated to 140° C. Trimethyl phosphite (397 g, 3.2 moles) was added in a steady stream during 1¼ hours. Upon complete addition, heating was continued for an additional four hours. Evolved methyl chloride was collected in a gas-wash bottle containing toluene, and was found to measure 135.6 g. Analysis by glpc, area %, indicated the reaction mixture contained 51% of the desired dichloroethenyl compound and 2% of the chloroethynyl impurity.

The reaction mixture was subjected to fractional distillation on a 12-inch Propack column and at a reflux ratio of up to 10:1, to give, in 14 fractions, 1461.41 g of product, bp 80°–105° C./2.5–10 mm Hg, containing 86% (1263 g) of methyl 3-(2,2-dichloroethenyl)-2,2-dimethylcyclopropanecarboxylate and 3% (50.1 g) of methyl 3-(chloroethynyl)-2,2-dimethylcyclopropanecarboxylate (glpc area %). Combination of appropriate fractions would give following product profile:

EXAMPLE 2

A sample of 2181 g of crude methyl 3-(2,2-dichloroethenyl)-2,2-dimethylcyclopropanecarboxylate, shown by glpc analysis to contain 70% (1520 g), based on an internal standard, of methyl 3-(2,2-dichloroethenyl)-2,2-dimethylcyclopropanecarboxylate and 3% (65 g, 0.35 mole), based on area %, of methyl 3-(chloroethynyl)-2,2-dimethylcyclopropanecarboxylate, was heated to 140° C. with stirring.

Trimethyl phosphite (43.5 g, 0.35 mole) was added in a steady stream during 15 minutes. Upon complete addition, the mixture was stirred for an additional 4 hours at 137°–141° C.

The reaction mixture was subjected to fractional distillation on a 12-inch Propack column and at a reflux ratio of up to 10:1 to give, in 13 fractions, 1757.2 g of product, bp 102°–115° C./10 mm Hg. Analysis by glpc (area %) indicated the product to be comprised of 87% (1528 g) of methyl 3-(2,2-dichloroethenyl)-2,2-dimethylcyclopropanecarboxylate and 1.6% (27.80 g) of methyl 3-(chloroethynyl)-2,2-dimethylcyclopropanecarboxylate. The apparent recovery of more dichloroethenyl compound than indicated to be present at the outset is attributed to the use of different methods of measurement (with and without an internal standard) in the two glpc determinations. Combination of appropriate fractions would give the following product profile:

|  |  |  |  | glpc area % | |
|---|---|---|---|---|---|
| Fraction | Wgt(g) | BP(°C.) | Reflux Ratio | (a) $Cl_2C=CH-$ | (b) $Cl-C\equiv C-$ |
| 1–2 | 233 | 102–106°/10mm Hg | 1:1/5:1/10:1 | 22 | 5 |
| 3–13 | 1524 | 108–115°/10mm Hg | 10:1/1:1 | 94 | 1 |

(a) methyl 3-(2,2-dichloroethenyl)-2,2-dimethylcyclopropanecarboxylate
(b) methyl 3-(chloroethynyl)-2,2-dimethylcyclopropanecarboxylate The following examples illustrate the effectiveness of the use of a phosphite to reduce the content of haloethynyl impurity in samples of dihaloethenylcyclopropanecarboxylate. Figures are given to show the percent haloethynyl compound present before and after reaction with phosphite. Distillation data are not given in these examples. Examples 3 and 4 relate to use of the present process on an industrial scale.

EXAMPLE 3

Crude ethyl 3-(2,2-dichloroethenyl)-2,2-dimethylcyclopropanecarboxylate was subjected to fractional distillation under vacuum, and lower boiling fractions were combined as a forecut. Gas liquid phase chromatography (glpc, area %) of a 113 kg sample of the forecut indicated it to be comprised of 48% (54.24 kg) of ethyl 3-(2,2-dichloroethenyl)-2,2-dimethylcyclopropanecarboxylate and 34% of ethyl 3-(chloroethynyl)-2,2-dimethylcyclopropanecarboxylate.

|  |  |  |  | glpc area % | |
|---|---|---|---|---|---|
| Fraction | Wgt(g) | BP(°C.) | Reflux Ratio | (a) $Cl_2C=CH-$ | (b) $Cl-C\equiv C-$ |
| 3 | 91 | 91°/10mm Hg | 1:1 | 14 | 6 |
| 4–7 | 253.7 | 96–104°/10mm Hg | 10:1 | 58 | 13 |
| 8–14 | 982.5 | 104–105°/10mm Hg | 10:1,6:1,2:1 | 99 | 1 |
| 15–16 | 134.2 | 80°/2.5–3mm Hg | 2:1 | 100 | 0 |

(a) methyl 3-(2,2-dichloroethenyl)-2,2-dimethylcyclopropanecarboxylate
(b) methyl 3-(chloroethynyl)-2,2-dimethylcyclopropanecarboxylate A 50 gallon glass-lined reactor equipped with a condenser was charged with the above sample of forecut (113 kg), and the contents were heated to 142° C. Triethyl phosphite (29.1 kg) was added during 4½ hours under a nitrogen atmosphere with stirring. The temperatures of the reaction mixture during addition of phosphite and throughout the course of the reaction was maintained in the range of 142° to 147° C. Evolved ethyl chloride was collected in a scrubber charged with 70 kg of absolute ethanol maintained at 0° to 5° C.

Heating was continued after complete addition of the triethyl phosphite for an additional 4 hours. Analysis (glpc, area%) of the reaction mixture showed 50% ethyl 3-(2,2-dichloroethenyl)-2,2-dimethylcyclopropanecarboxylate and 0.50% of ethyl 3-(chloroethynyl)-2,2-dimethylcyclopropanecarboxylate.

EXAMPLE 4

Crude ethyl 3-(2,2-dichloroethenyl)-2,2-dimethylcyclopropanecarboxylate was subjected to fractional distillation under vacuum, and lower boiling fractions were combined as a forecut.

A sample of the forecut (113 kg), assayed by glpc, area%, to contain 13% methyl 3-(2,2-dichloroethenyl)-2,2-dimethylcyclopropanecarboxylate and 57% of methyl 3-(chloroethynyl)-2,2-dimethylcyclopropanecarboxylate, was placed in a 50 gallon glass-lined reactor and heated to 145° C. Triethyl phosphite (56.7 kg) was added during 4 hours under a nitrogen atmosphere with stirring. The temperature of the reaction mixture during addition of the triethyl phosphite and throughout the course of the reaction was maintained in the range of 140° to 148° C. Evolved ethyl chloride was collected in a scrubber charged with 77 kg of absolute ethanol maintained at 0° to 5° C.

Heating was continued after complete addition of the triethyl phosphite for an additional 4 hours. Analysis (glpc, area%) of the reaction mixture indicated 13% methyl 3-(2,2-dichloroethenyl)-2,2-dimethylcyclopropanecarboxylate and 0.07% of methyl 3-(chloroethynyl)-2,2-dimethylcyclopropanecarboxylate.

EXAMPLES 5-13

The general procedure employed in these examples was similar to that described above for Examples 1-4. Reaction conditions and results of glpc analyses of the reaction mixtures for haloethynyl impurity before and after reaction with phosphite are summarized in the following table.

| Example | Molar Ratio $P(OR_3/CE^1$ | Reaction[2] Time (hr) | Reaction Temp. (°C.) | % CE (glpc area %) Before Reaction[3] | % CE (glpc area %) After Reaction |
|---|---|---|---|---|---|
| 5 | 2/1 | 4 | 150-175 | 3.0 | 0.2 |
| 6 | 1/1 | 2 | 125-168 | 54.0 | 5.2[4] |
| 7 | 1.1/1 | 2 | 140-165 | 54.0 | 1.5 |
| 8 | 1/1 | 2 | 136-155 | 27.0 | 4.0 |
| 9 | 1/1 | 4 | 138-150 | 3.7 | 1.1 |
| 10 | 1/5 | 4 | 140-150 | 26.0 | 19.3 |
| 11 | 1/1 | 2 | 140-148 | 3.8 | 1.3 |
| 12 | 1/1 | 2 | 136-141 | 26.0 | 3.4 |
| 13 | 1/1 | 1.17 | 138-141 | 11.0 | 2.6 |

[1]P(OR)₃ was triethyl phosphite in Examples 5-12 and trimethyl phosphite in Example 13; CE (chloroethynyl impurity) was ethyl 3-(chloroethynyl)-2,2-dimethylcyclopropanecarboxylate in Examples 5-12 and methyl 3-(chloroethynyl)-2,2-dimethylcyclopropanecarboxylate in Example 13; the dihaloethenylcyclopropanecarboxylate in Examples 5-12 was the ethyl ester, and in Example 13 the methyl ester.
[2]Reaction time does not include time for addition of phosphite.
[3]Crude dichloroethenyl compound before reaction with phosphite contains about 3-4% chloroethynyl impurity; distillation forecuts contain considerably more.
[4]Heating for an additional two hours reduced CE content to 4.6%.

I claim:
1. A process for reducing the content of a 3-(haloethynyl)cyclopropanecarboxylate impurity of the formula

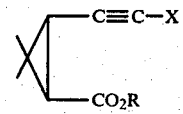

in a mixture containing the impurity and a 3-(2,2-dihaloethenyl)cyclopropanecarboxylate of the formula

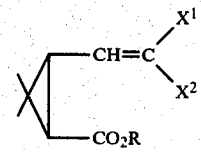

wherein $X^1$ and $X^2$ are the same or different, and each is a fluorine, chlorine, or bromine atom; X is a fluorine, chlorine, or bromine atom, and is the same as $X^1$ or $X^2$; and R is an alkyl group of 1 to 4 carbon atoms or is the residue $R^1$ of an alcohol $R^1OH$ wherein $R^1$ is a group of the formula

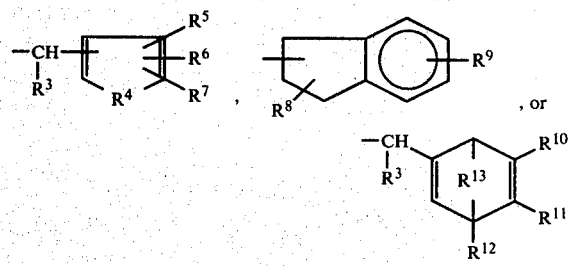

in which $R^3$ is hydrogen, lower alkyl, ethynyl, or cyano; $R^4$ is divalent oxygen, divalent sulfur, or vinylene; $R^5$, $R^6$, and $R^7$ are independently hydrogen, lower alkyl, halogen, lower alkenyl, phenyl, phenoxy, benzyl, phenylthio, or any two of $R^5$, $R^6$, and $R^7$ are joined to form a divalent methylenedioxy group attached to two adjacent ring carbon atoms of a phenyl ring, with the proviso that when $R^5$, $R^6$, or $R^7$ contains a phenyl ring such phenyl ring may be substituted with one to three substituents selected from halogen and lower alkyl; $R^8$ is hydrogen, lower alkyl, lower alkoxy, lower alkenyl, lower alkenyloxy, phenyl or benzyl; $R^9$ is hydrogen, halogen, lower alkyl, lower alkoxy, lower alkenyl, lower alkenyloxy, lower alkylthio, lower alkylsulfinyl, lower alkylsulfonyl, phenyl, phenoxy, benzoyl, nitro or cyano; $R^{10}$ and $R^{11}$, the same or different, are hydrogen, lower alkyl, halogen, cyano, lower alkyloxycarbonyl, or lower alkylaminocarbonyl; $R^{13}$ is an atom of oxygen or sulfur, $N—R^{14}$ where $R^{14}$ is hydrogen or lower alkyl, or a methylene group; and $R^{12}$ is phenyl, benzyl, or benzoyl, which may be substituted on the phenyl ring with halogen or lower alkyl, which comprises contacting said mixture with a phosphite of the formula $$P(OR^2)_3$$

wherein the $R^2$ groups are the same or different and each is an alkyl group of 1 to 6 carbon atoms or a phenyl group,
so that the phosphite and haloethynyl impurity chemically interact, and thereafter recovering the dihaloethenylcyclopropanecarboxylate from the reaction mixture.

2. The process of claim 1 wherein R is an alkyl group of 1 to 4 carbon atoms and the dihaloethenylcyclopropanecarboxylate is recovered from the reaction mixture by distillation.

3. The process of claim 2 wherein the mixture containing the haloethynyl impurity and dihaloethenylcyclopropanecarboxylate is contacted with the phosphite, and the whole reaction mixture is heated at an elevated temperature.

4. The process of claim 3 wherein the reaction mixture is heated at a temperature in the range of from about 125° to 175° C.

5. The process of claim 4 wherein the reaction mixture is heated at a temperature in the range of from about 140° to 150° C.

6. The process of claim 4 wherein R is a methyl or ethyl group.

7. The process of claim 4 wherein $X^1$ and $X^2$ are the same and each is a bromine or chlorine atom.

8. The process of claim 7 wherein $X^1$ and $X^2$ are chlorine atoms.

9. The process of claim 4 wherein the $R^2$ groups are the same and each is an alkyl group of 1 to 4 carbon atoms or a phenyl group.

10. The process of claim 9 wherein each $R^2$ is a methyl or ethyl group.

11. The process of claim 4 wherein at least one mole of phosphite is employed for each mole of haloethynyl impurity in the starting mixture.

12. A process for reducing the content of a 3-(chloroethynyl)cyclopropanecarboxylate impurity of the formula

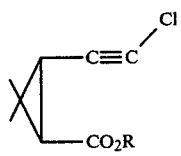

in a mixture containing the impurity and a 3-(2,2-dichloroethenyl)cyclopropanecarboxylate of the formula

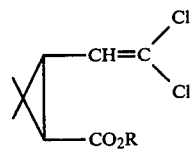

wherein R is an alkyl group of 1 to 4 carbon atoms, which comprises contacting said mixture with a phosphite of the formula $$P(OR^2)_3$$

wherein the $R^2$ groups are the same and each is an alkyl group of 1 to 4 carbon atoms or a phenyl group, heating at a temperature in the range of from about 125° to 175° C. so that the phosphite and chloroethynyl impurity chemically interact, and thereafter recovering the dichloroethenylcyclopropanecarboxylate from the reaction mixture by distillation.

* * * * *